United States Patent [19]

Yewer, Jr.

[11] Patent Number: 5,586,969
[45] Date of Patent: Dec. 24, 1996

[54] REVERSIBLE SUPPORT BELT

[76] Inventor: Edward H. Yewer, Jr., 6259 N. Highway 83, Hartland, Wis. 53029

[21] Appl. No.: 490,928

[22] Filed: Jun. 16, 1995

[51] Int. Cl.⁶ .................................................. A61F 5/00
[52] U.S. Cl. .................. 602/19; 128/101.1; 128/99.1; 2/311
[58] Field of Search ........................... 2/311, 312, 313, 2/338, 44, 45; 602/5, 19; 128/95.1, 96.1, 99.1, 100.1, 101.1

[56] References Cited

U.S. PATENT DOCUMENTS

| | | |
|---|---|---|
| 75,737 | 3/1868 | Crocker . |
| 882,181 | 3/1908 | Thomas . |
| 1,174,757 | 3/1916 | Packer ........................ 602/19 |
| 2,181,689 | 11/1939 | Bell . |
| 2,543,416 | 2/1951 | Mergehenn . |
| 2,554,337 | 5/1951 | Lampert ...................... 602/19 X |
| 2,671,904 | 3/1954 | Stroh .......................... 2/311 |
| 3,561,436 | 2/1971 | Gaylord, Jr. ............... 602/19 |
| 3,568,670 | 3/1971 | Gaylord, Jr. . |
| 3,578,773 | 5/1971 | Schultz ....................... 602/19 |
| 3,603,316 | 9/1971 | Lehman . |
| 4,384,372 | 5/1983 | Rector ....................... 602/19 X |
| 4,572,167 | 2/1986 | Brunswick . |
| 4,576,154 | 3/1986 | Hyman et al. .............. 602/19 |
| 4,747,399 | 5/1988 | Glomstead . |
| 4,782,535 | 11/1988 | Yewer, Jr. et al. . |
| 4,794,916 | 1/1989 | Porterfield et al. ........ 602/19 |
| 4,833,730 | 5/1989 | Nelson . |
| 4,884,562 | 12/1989 | Stone ......................... 602/19 |
| 4,907,576 | 3/1990 | Curlee . |
| 4,964,401 | 10/1990 | Taigen . |
| 5,036,864 | 8/1991 | Yewer, Jr. . |
| 5,046,488 | 9/1991 | Schiek, Sr. . |
| 5,178,163 | 1/1993 | Yewer, Jr. . |
| 5,188,586 | 2/1993 | Castel et al. .............. 602/19 |
| 5,207,636 | 5/1993 | Striano . |
| 5,269,050 | 12/1993 | Yewer, Jr. . |
| 5,316,022 | 5/1994 | Schiek, Sr. . |
| 5,388,274 | 2/1995 | Glover et al. ............. 602/19 X |
| 5,421,809 | 6/1995 | Rise ........................... 602/19 |
| 5,445,601 | 8/1995 | Harlow ....................... 602/19 |
| 5,447,498 | 9/1995 | Watson ....................... 602/19 |
| 5,464,136 | 11/1995 | Eddy .......................... 2/311 X |
| 5,503,620 | 4/1996 | Danzger ..................... 602/19 |

*Primary Examiner*—Linda C. Dvorak
*Attorney, Agent, or Firm*—Quarles & Brady

[57] ABSTRACT

A two piece reversible support belt has a body and a strap. The body is longitudinally curved so that when it is wrapped around a human waist it forms a tapered shape, and may be worn so that the tapered shape either opens up or opens down. The strap encircles the body and is detachably removable from the body so that the free end of the strap may always be held in the right hand by a man or in the left hand by a woman, regardless of which orientation the body is worn in. In one form, lateral slits are cut in the body to retain the strap laterally, and the strap may be worn against either side of the body in this embodiment. Detachable fastener material may be provided on the inside surface of the strap in this embodiment and an accessory such as a lumbar pad may be secured thereby, between the belt body and the wearer. The body may also be made articulated with elastic hip sections or with molded foam accordion fold hip sections. Belt loops may also be molded into the belt body, or separately molded in two halves and put together to sandwich the body material between peripheral flanges of them. The body may be made with a laminate of foam and fabric or of foam and a continuous surface film or foil, and may be made with or without hip notches along one or both side edges.

16 Claims, 8 Drawing Sheets

REVERSIBLE SUPPORT BELT

BACKGROUND OF THE INVENTION

1. Field of the Invention

This invention relates to abdominal support belts, and in particular to such a belt which is specially adapted for use as either a tool support belt or as an abdominal support belt.

2. Discussion of the Prior Art

Belts for suspending tools from the waist of a human wearing the belt are known. For example police officers wear such belts and they suspend from them implements such as a gun, handcuffs, bullets, keys, a walkie-talkie, a baton and other items. Also, workmen such as construction workers often wear belts of a similar nature from which they suspend tools such as hammers, screw drivers, wrenches, pry bars, etc.

Such tool belts, because they are for the express purpose of supporting weight, have been made in a conical shape which opens downwardly so as to distribute the weight of the tools on top of the hips or pelvic bones of the human body so as to conform to that area of the body.

However, because the waist area is generally hour-glass shaped, it is sometimes desirable and is known that abdominal support belts, such as weight lifting belts of the type that are intended to increase the intra-abdominal pressure of a human body and therefore increase its load carrying capability, are worn higher up on the body and therefore may be in the general shape of a cone which opens upwardly. Heretofore, straight belts have been made which could be used for either purpose out of a polymeric memory foam material which would conform to the waist, regardless of whether the belt was worn higher or lower on the waist. A belt can also be made conical to further conform, for example for extreme hourglass figures, either opening up or opening down. If conically shaped, the belt was better if worn in only one orientation, as either a tool support belt or as an abdominal support belt, since the buckle of the belt could not be switched from one side to the other. In other words, since it is customary for a man to hold the buckle in his left hand when putting on a belt, if the belt were turned upside down, the buckle would be in the man's right hand, which to some is unnatural. Also, physically challenged people or amputees can sometimes benefit from being able to switch the side of a buckle in a belt. Thus, the need exists for a belt which works well as either a tool support belt or as an abdominal support belt, and in which the side of the buckle can be changed.

SUMMARY OF THE INVENTION

The invention satisfies this need in a support belt for wearing around the waist of a human body of the type having a body with an inner surface, an outer surface and longitudinal side edges connecting the inner and outer surfaces, and a cinching strap narrower than the body and having an inner surface, an outer surface and longitudinal side edges connecting the inner and outer surfaces for encircling the body when the belt is worn around the waist of a human body. The strap is detachably secured to the body, and the body retains the strap in the proper lateral position.

In a preferred form, longitudinal side edges of the body are arcuate over the length of the body and curve in the same direction so that one of the edges is shorter than the other edge. The strap can be detached from the body and includes at least two relatively inextensible and straight strips joined end to end by an intermediate bridging section which is flexible so as to allow the strips to form an angle relative to one another as the strips lay against the body. Thus, the body is conical when wrapped around the wearer's waist, and may be worn with the cone either opening up or opening down.

In one form the body is provided with belt loops on its exterior surface to hold the strap while allowing the strap to pass through the loops at an angle, so that the strap may conform to the curved shape of the body. In another form, hook and loop type fastener material detachably secures the strap to the body and is of a sufficient width so that the strap can traverse the body at an angle and be detachably secured thereto.

In another form, the body of the belt is perforated so as to define belt loops between the perforations. In this form, the body may be worn with either side out, since the belt loops can retain the strap on either side of the body. Detachable fastener material may be provided on the inside of the strap, which can secure a lumbar pad or other accessory between the body and the wearer.

In addition, the body may be made articulated, having one or more laterally flexible sections incorporated into it, so as to increase the lateral flexibility of the body.

Other objects and advantages of the invention will be apparent from the detailed description and from the drawings.

DETAILED DESCRIPTION OF THE PREFERRED EMBODIMENTS

FIGS. 1–8 illustrate a first embodiment of a belt 10 of the invention. The belt 10 includes a body 12 and a cinching strap 14. The body 12 is preferably of a foam and fabric laminated construction of the type disclosed in any of U.S. Pat. Nos. 4,782,535, 5,036,864, 5,178,163 or 5,269,050, the disclosures of which are hereby incorporated by reference. Alternatively, the body 12 may be any other suitable construction for making tool or abdominal support belts, for example, leather.

Figure 18:
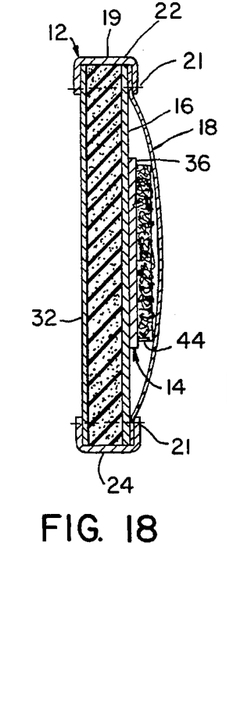
FIG. 18 is a sectional view as viewed from the plane of the line 18—18 of FIG. 3.

A distinction of the body 12 over the belt bodies disclosed in the aforementioned patents is that it has sewn against its exterior surface 16 (See FIG. 18) nylon belt loop straps 18 which are circumferentially spaced apart and run generally vertically for the entire width of the body 12, through which the strap 14 is threaded. The straps 18 have their ends extending under the edge binding 19 so that the same stitching which secures the edge binding, shown at 21, also secures the straps 18. The loops 18 hold the strap 14 adjacent to the exterior surface 16 of the body 12 when the strap 14 is released, and allow it to traverse the body 12 at an angle (FIGS. 3 and 5) so as to conform to the curved shape of the body 12.

Figure 1:
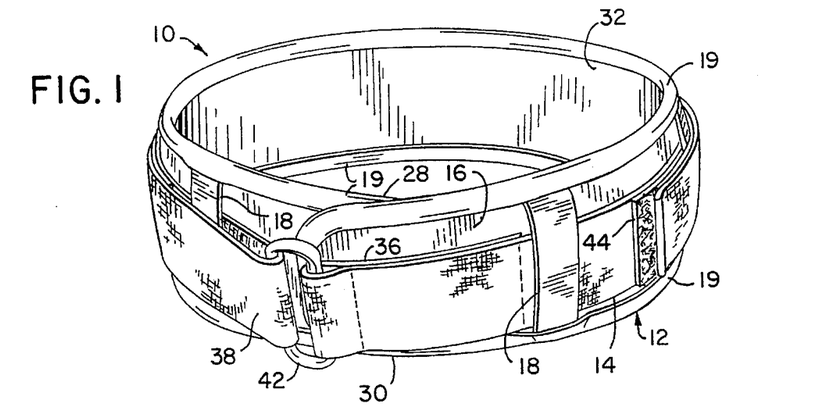
FIG. 1 is a front perspective view of a support belt of the invention.
Figure 2:
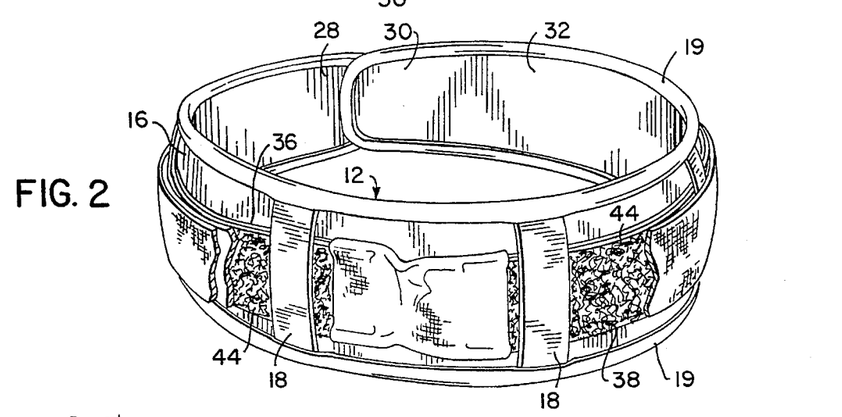
FIG. 2 is a rear perspective view of the belt of FIG. 1.
Figure 3:
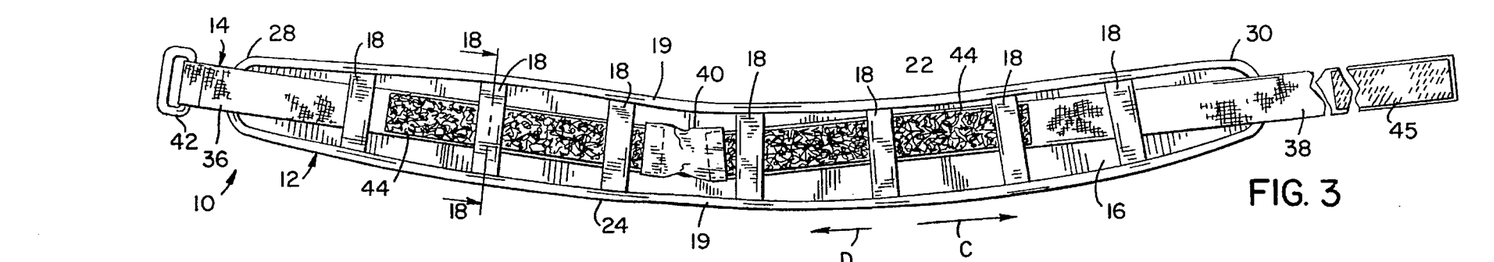
FIG. 3 is an exterior side plan view of the belt of FIG. 1 opened up and laid flat.
Figure 4:
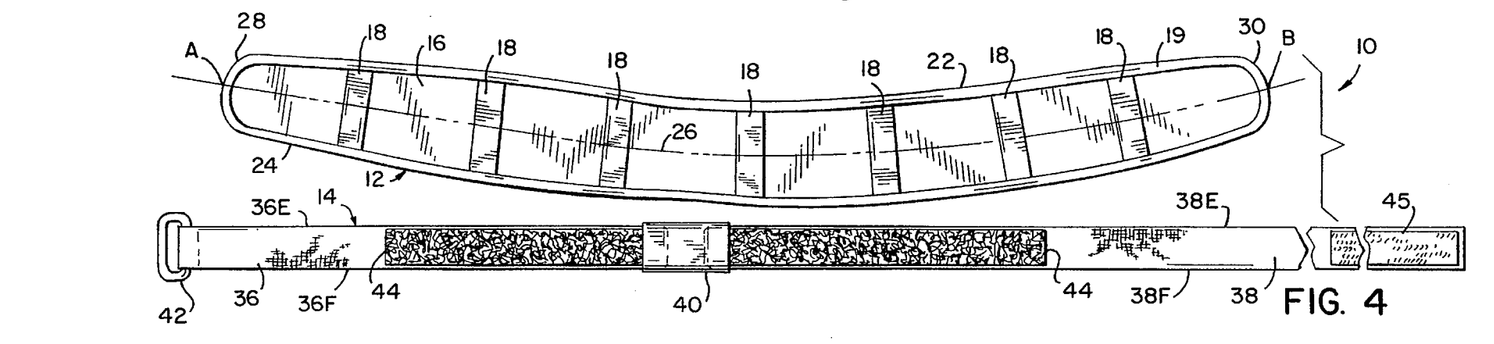
FIG. 4 is a view similar to FIG. 3 but with the body and strap of the belt disassembled from each other and both laid flat.
Figure 5:
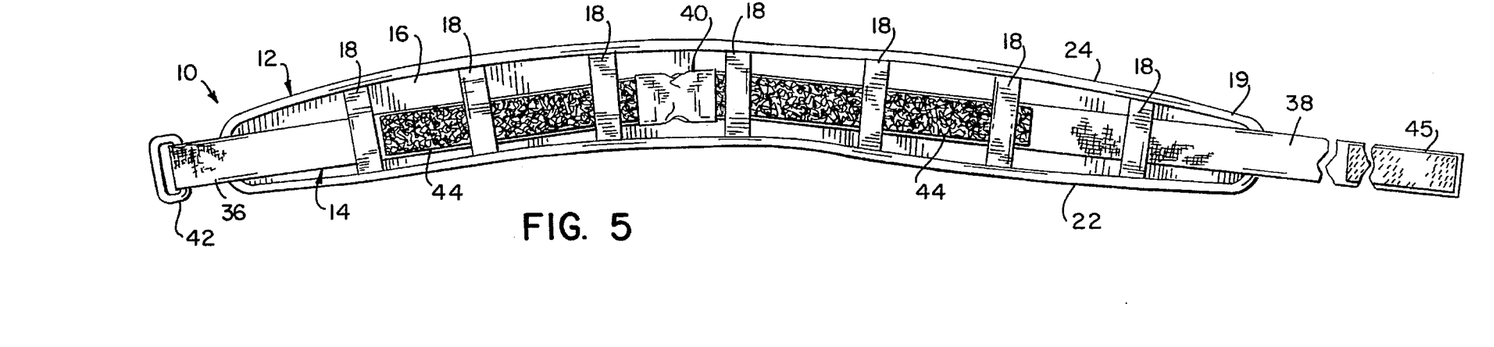
FIG. 5 is a view similar to FIG. 3 but with the body reversed in orientation relative to the strap.
Figure 17:
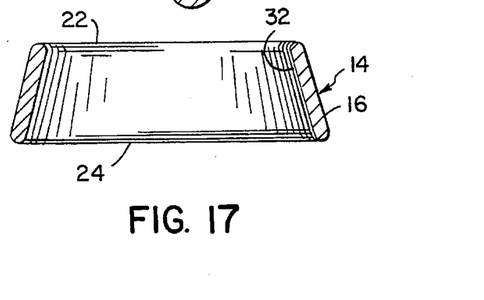
FIG. 17 is a sectional view illustrating the conical shape of a belt of the invention when it is wrapped around the waist of a human.

As best shown in FIGS. 3–5, the body 12 also differs from the bodies disclosed in the aforementioned patents in that its side edge 22 as measured in length from point A to point B is shorter than its side edge 24 as measured between the same two points. Points A and B are where the longitudinal center line 26 of the body intersects the extreme ends of the body 12. Thus, the side edges 22 and 24, as well as the longitudinal axis 26, are concavely curved in the same direction. As a result, as shown in FIG. 17, when the body 12 is wrapped in a circle or oval, as it is around the waist of a human, so that its ends 28 and 30 overlap, its inner surface 32 and exterior surface 16 assume the general shape of a cone in that they taper between the side edges, with side edge 22 having a smaller circumferential dimension than the circumferential dimension of the side edge 24, for 360° around the belt.

The tapering shape of the wrapped around body 12 may be oriented with either the side edge 22 above or below the side edge 24. If the belt 10 is to be worn as a tool support belt, with tools suspended from the strap 14 between the belt loops 18 and the belt supported on the wearer's hips, it is usually desirable for the wearer to wear the body 12 in the orientation with the side edge 22 above the side edge 24, so that the tapering shape opens downwardly. However, if the belt 10 is to be used so as to increase the intra-abdominal pressure of the body, for example in weight lifting, it may be desirable to wear the belt with side edge 24 above side edge 22, so that the tapering shape opens upwardly, and to wear the belt above the hips.

For the belt to be able to be comfortably put on and worn in either orientation, the strap 14 is able to be threaded through the belt loops 18 in either direction. This is because, for mens' belts, the buckle is customarily held in the left hand, and for women's belts the buckle is usually held in the right hand. FIG. 3 illustrates the strap 14 threaded through the loops 18 in the direction C and FIG. 5 illustrates the strap 14 threaded through the loops 18 in the opposite direction D.

Figure 6:
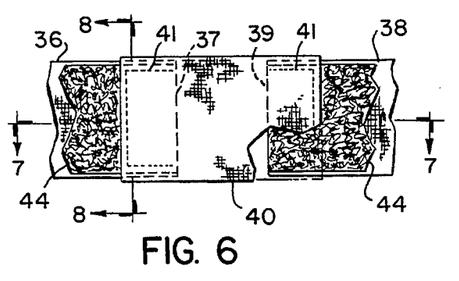
FIG. 6 is a fragmentary plan view of a portion of the strap shown in FIGS. 1–5.
Figure 7:
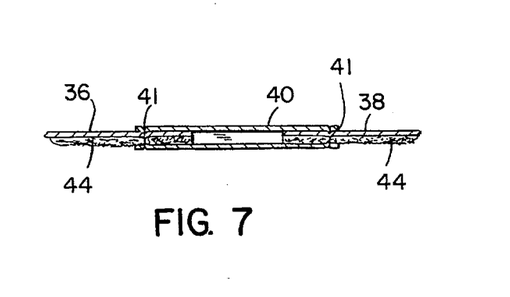
FIG. 7 is a sectional view taken along the plane of the line 7—7 of FIG. 6.
Figure 8:
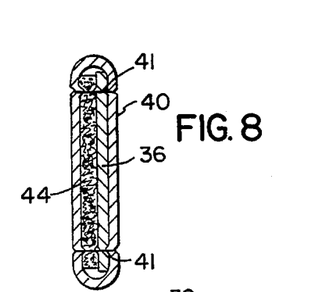
FIG. 8 is a sectional view taken along the plane of the line 8—8 of FIG. 6.
Figure 9:
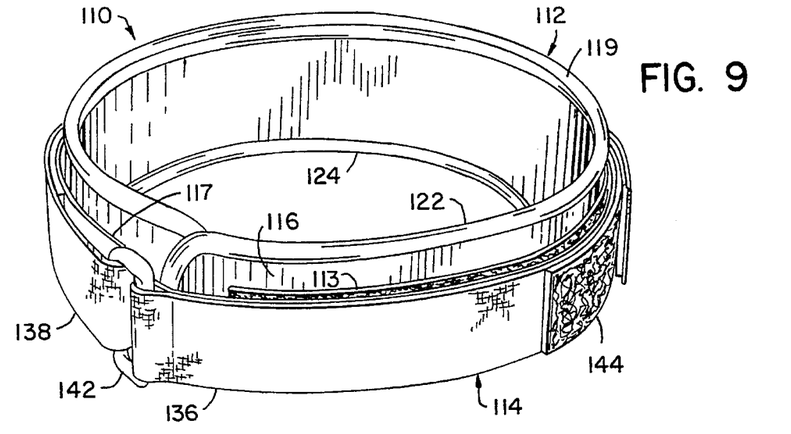
FIG. 9 is a front perspective view of a second embodiment of a support belt of the invention.
Figure 10:
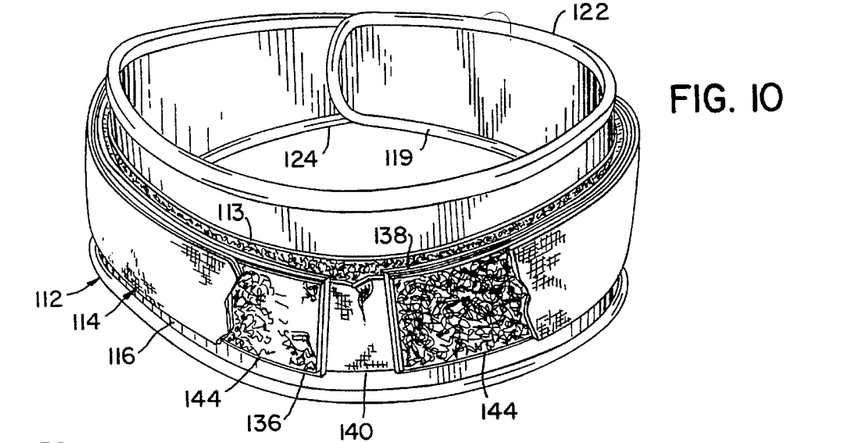
FIG. 10 is a rear perspective view of the belt of FIG. 9.
Figures 11, 12:
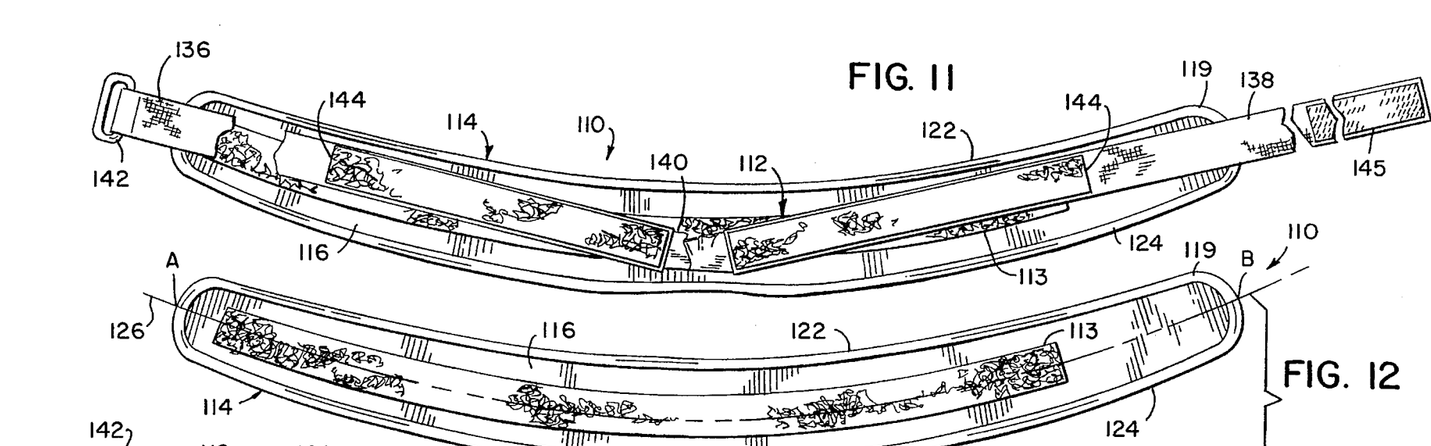
FIG. 11 is a exterior side plan view of the belt of FIG. 9 opened up and laid flat.
FIG. 12 is a view similar to FIG. 11 but with the strap disassembled from the body of the belt and showing the exterior surfaces of the strap and body.
Figures 13, 14:
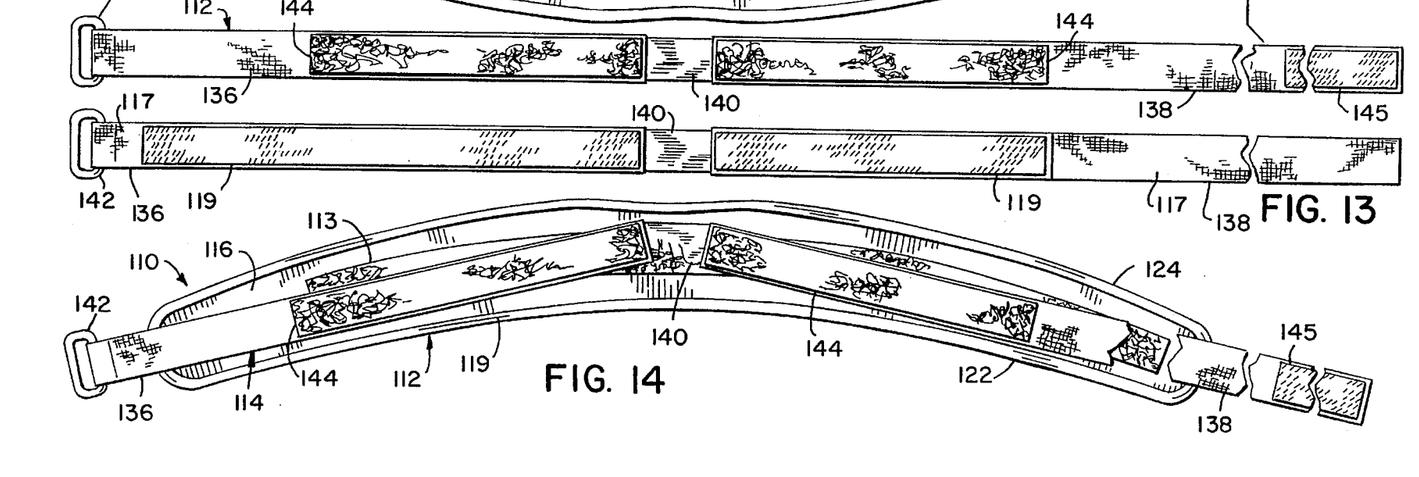
FIG. 13 is a plan view of the strap opened up and laid flat showing the interior surface of the strap.
FIG. 14 is a view similar to FIG. 11 but with the body reversed in orientation relative to the strap.
Figure 15:
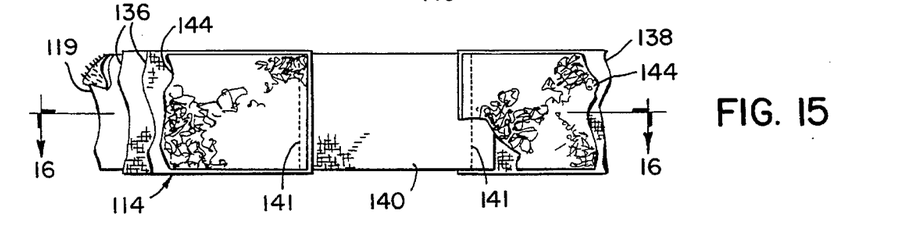
FIG. 15 is a fragmentary plan view of a portion of the strap illustrated in FIGS. 9–14.

As best shown in FIGS. 6–8, the strap 14 is made from two strips, 36 and 38, which are connected at their inside ends 37 and 39 by a bridging section 40. A ring 42 is secured at the outer end of strap 36 by the strap 36 being threaded through the ring 42, doubled back and stitched to itself. Hook and loop type fastener material is secured on the outer surfaces of the strips 36 and 38 at 44 and mating hook and loop type fastener material is secured on the inner surface at the outer end of strip 38 at 45 so that after the outer end of strip 38 is threaded through the hook 42, it can be doubled back and attached to one of the sections 44, so as to keep it from dangling.

Each of the strips 36 and 38 is made from a heavyweight woven nylon strapping material approximately two inches in width, as is described for the material of the straps in the aforementioned U.S. patents. This material is extremely strong and for all practical purposes is inextensible when used as a belt strap as in the invention. The side edges 36E and 36F (FIG. 4) are straight and of the same length and the side edges 38E and 38F are straight and of the same length. Thus, whereas each of the strips 36 and 38 is straight, and body 12 is curved, unless some accommodation was made, the shape of the strips 36 and 38 would not conform to the shape of the body 12.

To make the strap 14 conform to the longitudinal curved shape of the body 12, bridging section 40 is provided, which is a sleeve-like piece of fabric material of a high tensile strength, but which is flexible. This material may be, for example, cotton, nylon, Kevlar™, hook compatible material or any other suitable flexible cloth material. The inward ends of the strips 36 and 38 are inserted into the tube-like flexible fabric bridging section 40, and stitched thereto as shown in FIGS. 7 and 8 at 41, with the ends of the strips 36 and 38 spaced apart. Bridging section 40 need not be elastic, so long as it is not rigid and allows the straps 36 and 38 to assume an angle relative to one another in the plane of the straps 36 and 38 (i.e., a lateral plane) as shown in FIGS. 3 and 5.

FIGS. 9–16 illustrate a second embodiment of a belt 110 of the invention. Elements of the belt 110 corresponding to elements of the belt 10 are labeled with the same reference number plus 100.

The body 112 is essentially the same as the body 12 except for the fact that the body 112 does not have any belt loops, but instead is provided with a strip 113 of hook and loop type fastener material on its exterior surface 116. The inside surface 117 of strap 114 is provided with mating hook and loop type fastener material 119 (FIGS. 13 and 16) which mates with the fastener material 113 so as to secure the inside surface 117 of the strap 114 against the outside surface 116 of the body 112. The fastener material 113 and 119 is wide enough to allow the strap 114 to traverse the body 112 at an angle with sufficient overlapping area so as to secure the body 112 and strap 114 together.

Figure 16:
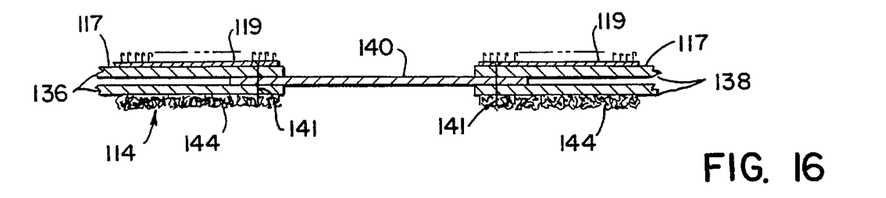
FIG. 16 is a sectional view taken along the plane of the line 16—16 of FIG. 15.

The strap 114 also differs from the strap 14 in that the bridging section 140 in the strap 114 is not a tubular sleeve of material, but instead is a single layer web of elastic material whose opposed ends are stitched to the inner ends of the straps 136 and 138. This elastic material is preferably a woven or knit elastic fabric of a suitably high tensile strength, for example of the type which is commercially available from Jessica Trimming located in Hialeah, Fla. As shown in FIG. 16, the opposed ends of the straps 136 and 138 may be made in two plies, with one sewn against each side of the bridging section 140. By using hook and loop type fastener material to secure the strap 114 to the body 112, the tensile strength of the body 112 may be utilized to help react against the tensile stress exerted upon the strap 114 by the user when he or she cinches the strap 114 around his or her waist, thereby reducing the tensile stress exerted on the section 140.

Figure 19:
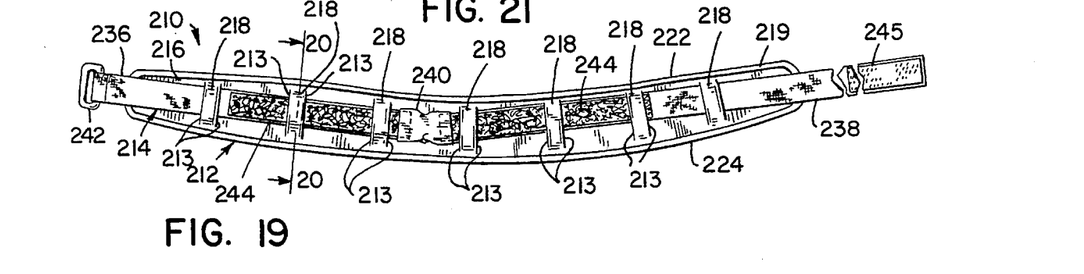
FIG. 19 is a view similar to FIG. 3 but of an alternate embodiment of a belt of the invention.
Figure 20:
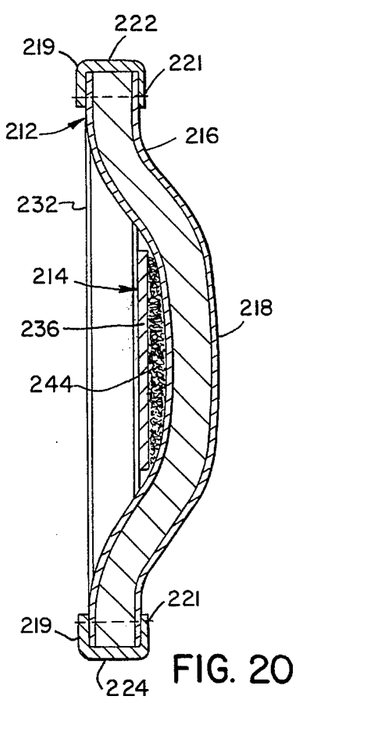
FIG. 20 is an enlarged sectional view as viewed from the plane of the line 20—20 of FIG. 19.

Since the strap 114 may be removed from the body 112 and reversed with respect to it, so that the body 112 may be worn so that its tapered shape opens either up or down, the belt 110 is said to be reversible. A third embodiment 210, shown in FIGS. 19–20, is reversible in this manner, and is also reversible in a second way, in that it can be worn with either one of its surfaces toward the wearer. It is therefore said to be two-way reversible. Elements of the belt 210 corresponding to elements of the belt 10 are labeled with the same reference number plus 200.

The strap 214 may be made like either the strap 14 or the strap 114, or any other similar construction in which two relatively laterally rigid belt sections are joined by a laterally flexible section so as to be laterally articulatable. If made like the belt 114, the inside hook and loop fastener material 119 may be omitted, since the belt 210 has belt loops 218 to hold the strap 214 on.

The body 212 differs in construction from either the body 12 or the body 112 in that the belt loops 218 are defined by axially spaced laterally extending lines of perforation 213 which extend through the thickness of the body 212, and are spaced inward from the side edges of the body 212. As such, the belt loops 218 may be bowed out of the plane of the body 212 to either side, so that they may function to secure the strap 214 against either side of the body 212. Thus, the body 212 may be worn with either one of its sides 216 or 232 facing the wearer, or stated another way, with either one of its sides 216 and 232 facing outward.

This possibility presents the opportunity to make the body 212 with different colors or patterns on its two sides 216 and 232, to give the wearer an option when wearing the belt. This is in addition to the option presented by all of the aforementioned embodiments that is afforded by providing the strap 14, 114 or 214 separate from the respective body 12, 112 or 212, which is to allow the same strap to be used with different bodies, which may differ, for example, in appearance, width, length or stiffness. Thus, a belt of the invention may be sold as a kit, with one strap and multiple bodies, any one of which may be secured with the strap. Several straps can also be provided of different types which are interchangeable with the various bodies, for example one like the strap 14 illustrated and one like the torque ring type strap disclosed in U.S. Pat. No. 5,036,864, which is incorporated herein by reference.

Figure 21:
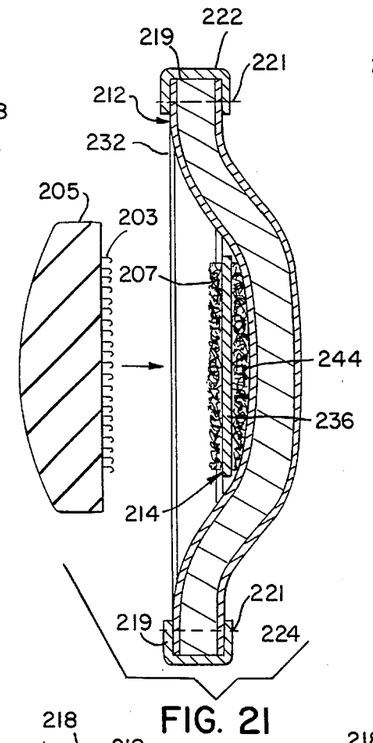
FIG. 21 is a view similar to FIG. 20 but showing a modification of the strap and a detachable accessory lumbar pad.

It should also be noted that with the loops 218, spaced areas of the strap 214, i.e., the areas where the strap underlies the loops 218, are against the wearer. This presents the opportunity, as illustrated in FIG. 21, to provide hook and loop fastener material 207, preferably of the softer loop type as shown, on the inner surface of the strap 214 so that this material is facing the wearer in these areas. A lumbar pad 205, insulating pad or other detachable accessory may be provided with mating hook and loop fastener material 203 so as to be secured against these areas, and provide another option for the wearer. Alternatively, a belt loop could be provided on the pad 205 or other accessory through which the strap 214 could be threaded to secure the accessory.

Figure 22:
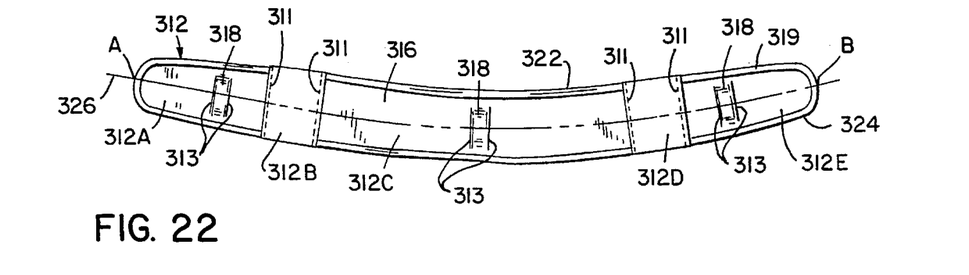
FIG. 22 is a side plan view of an alternate body for a belt of the invention.

FIG. 22 illustrates a fourth embodiment 312 of a body for a belt of the invention. The body 312 is similar to the body 212 in that it has slits 313, or lines of perforation, which define belt loops 318, although only three loops 318 are provided, which is adequate to keep the strap (not shown, but similar to any of the previously described straps) positioned laterally relative to the body 312. Elements of the body 312 corresponding to elements of the body 212 are labeled with the same reference number plus 100.

The body 312 is made in five sections which are stitched together in end to end fashion, as indicated at 311. The end and central sections 312A, 312C and 312E are made of the same material as the bodies 12, 112 and 212, i.e., a relatively laterally stiff foam and fabric laminate. The bridging sections 312B and 312D are preferably made of a laterally flexible material, such as the material of the bridging section 140 in the strap 14 and it may be elastic as is the bridging section 140 in the strap 114. Preferably, the sections 312B and 312D are positioned, relative to the sections 312A, C and E, at the sides of the wearer, on or above the hips. This construction allows the ends 312A and E to laterally articulate relative to the center or back 312C for increased flexibility. The strap for the body 312 is preferably an articulated one like the straps 14, 114 or 214, as previously described, but need not be articulated, depending on the curvature of the body 312. Note that the strap completely surrounds the articulated body and limits its expansion, since the strap 14 is for all practical purposes inextensible, whereas the body 312 would normally not be worn at the limit of its extension.

FIGS. 23–26 illustrate an alternate way of making a belt body articulated, like the body 312. In the belt 412, the foam and fabric laminated material of the belt is hot compression molded to have the accordion fold structure 439 illustrated in FIG. 24. Thus, in this structure, no separate elastic panels are needed to be sewn into the body, the desired elasticity being provided by the accordion folds of the foam material itself, and all five sections 412A–E of the belt are integral with one another. Elements of the belt 412 corresponding to elements of the belt 312 are identified by the same reference number plus 100.

Figure 23:
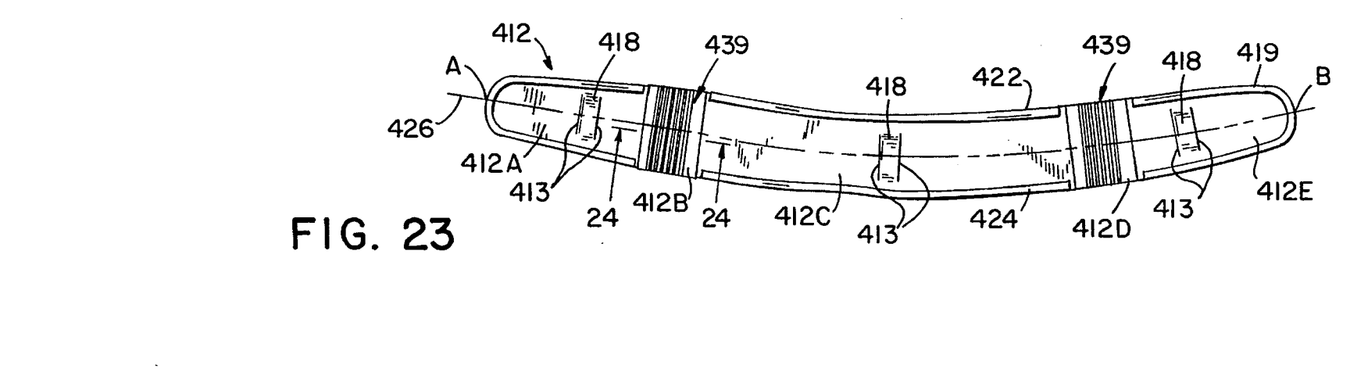
FIG. 23 is a side plan view of another alternate body for a belt of the invention.

The foam material of the body 412 may be any suitable heat moldable foam, such as polyethylene, which may or may not be laminated on one or both sides to a fabric layer. A suitable material is described, for example, in U.S. Pat. No. 5,178,163, incorporated by reference, and the material may or may not be perforated as described in U.S. Pat. No. 5,178,163.

For such molding, the foam or foam and fabric laminate is first heated in an oven to a temperature in the range of 250–350° F., after which it is placed in a press to form the accordion folds at a pressure sufficient to yield the desired thickness for approximately 5–10 minutes, until the foam cools sufficiently to take on a permanent set in that shape, after which the piece is cut to the desired shape. The resulting material is longitudinally resilient and able to conform to a person's particular shape in the area of the hips and waist.

Figures 24, 25, 26, 27:
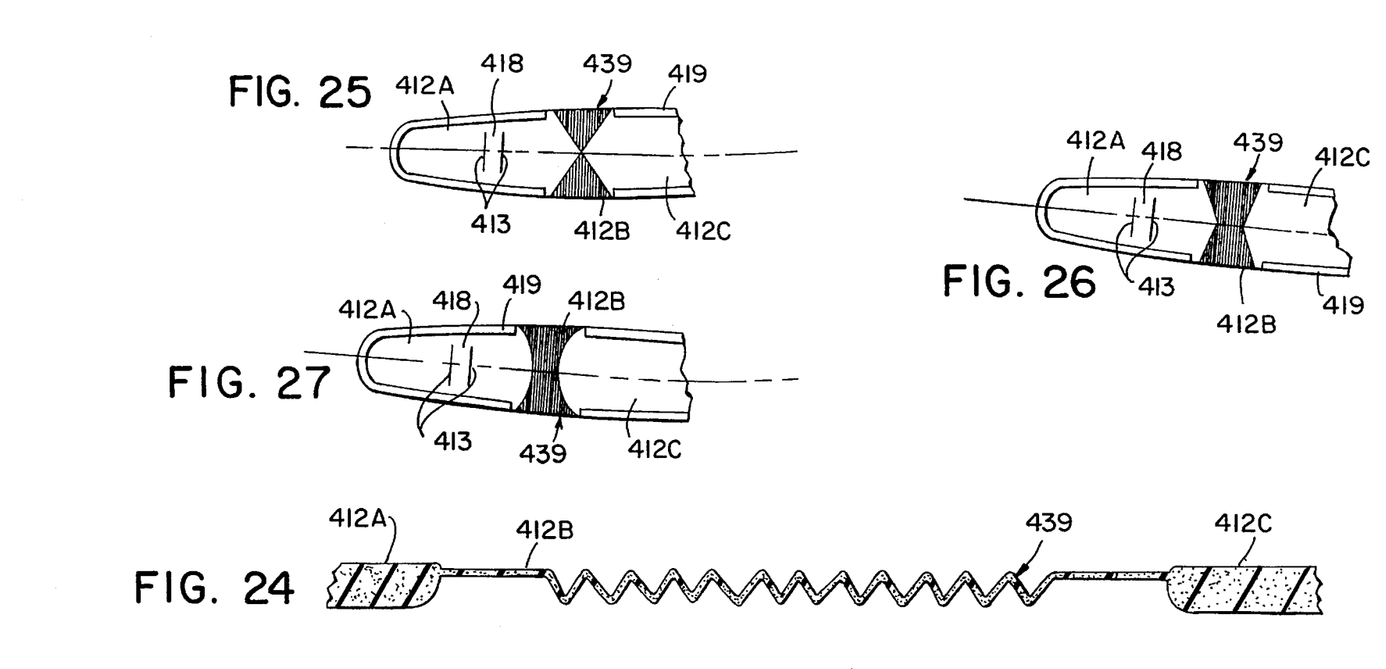
FIG. 24 is a cross-sectional view as viewed from the plane of the line 24—24 of FIG. 23.
FIG. 25 is a fragmentary plan view of a variation on the body of FIG. 23.
FIG. 26 is a fragmentary plan view of a second variation on the body of FIG. 23.
FIG. 27 is a fragmentary plan view of a third variation on the body of FIG. 23.

FIGS. 25–27 illustrate other patterns for the molded accordion fold structure 439, which place greater lengths of folds near the edges of the body, to yield greater axial rigidity but still allow stretching at the edges to conform to the human shape.

Figure 28:
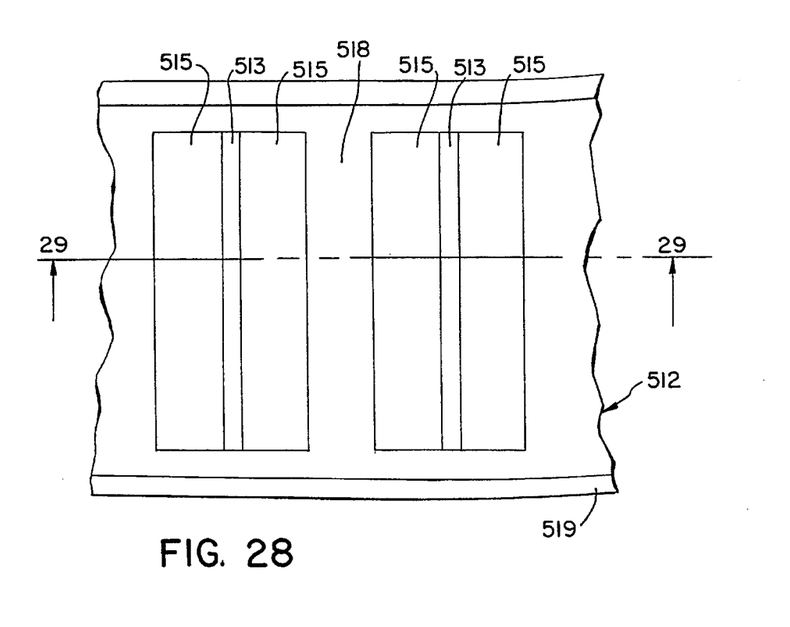
FIG. 28 is a fragmentary plan view of a belt loop which has been molded into a belt body to practice the invention.
Figure 29:
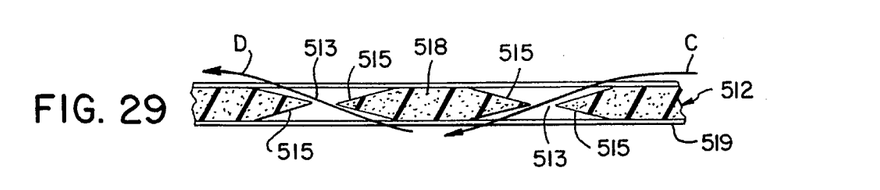
FIG. 29 is a cross-sectional view as viewed from the plane of the line 29—29 of FIG. 28.
Figure 30:
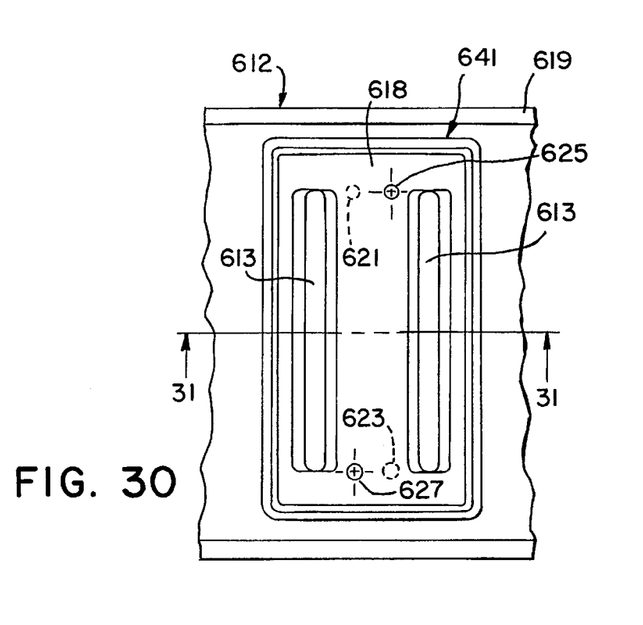
FIG. 30 is a fragmentary plan view of a belt of the invention having a molded plastic or rubber belt loop.
Figure 31:
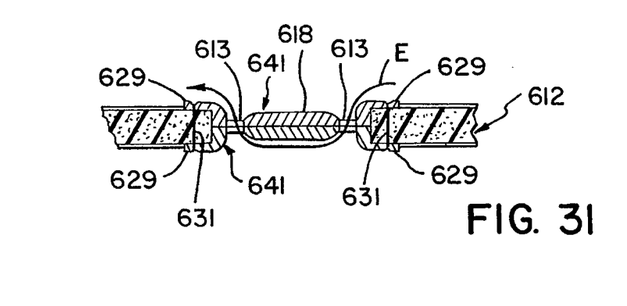
FIG. 31 is a cross-sectional view as viewed from the plane of the line 31—31 of FIG. 30.
Figure 32:
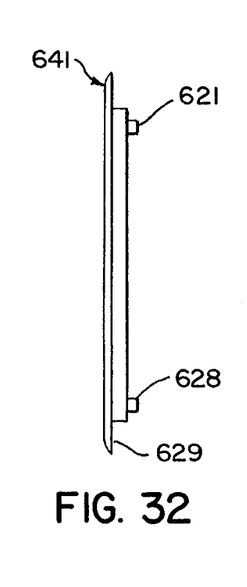
FIG. 32 is a side plan view of half of the molded belt loop of FIG. 30.
Figure 33:
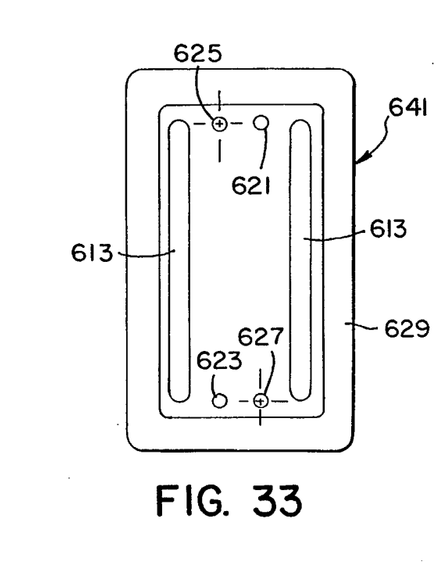
FIG. 33 is a rear plan view of the belt loop half of FIG. 32.

FIGS. 28 and 29 illustrate an alternate way of providing belt loops in a body of the invention. Whereas the loops 18 are provided by slits 13, the loops 518 are heat molded into the belt body, using a hot foam molding process like that described above, except that it forms slits 513 in which the foam has been totally squeezed out to form a void, rather than accordion folds. The strap would be threaded through the slits 513 as indicated by the arrows C and D. Tapered transition regions 515 are molded adjacent to the slits 513 to smooth the entry and exit of the strap as it threads its way through the loop 518, for the comfort of the user and to give a more finished appearance to the belt.

Another alternate way of providing belt loops in a belt of the invention is illustrated in FIGS. 30–33. In this belt 612, loops 618 are provided by two identical molded plastic halves 641, which are snapped or friction fit by their posts 621 and 623 fitting into the respective holes 625 and 627 of the other half. The halves 641 could also be secured together by any other suitable means, for example, by a glue, adhesive or ultrasonic weld. A rectangular hole is cut in the material of the body 612, and the periperal flanges 629 of the halves 619 sandwich the edges of the hole between them. Stitching 631 through the flanges and the body material secures the halves 619 in place. The halves 619 are preferably molded from a soft plastic or elastomer which approximates the stiffness of the material of the body 612, i.e., four pound "A" grade ¼ inch thick closed cell radiation cross-linked polyethylene foam in the preferred embodiment, so that they may be stitched, do not gouge into the user's body, and provide a uniform function and feel. By providing the loops 618 with two halves, one of the halves may be inserted into the hole in the body from the inside and the other half may be inserted from the outside, so as to sandwich the body material around the edges of the hole and ready the assembly for stitching, to provide a secure fixation of the halves to the body material. Arrow E indicates how the strap is threaded through the slots 613 of the loop 618.

Figure 34:
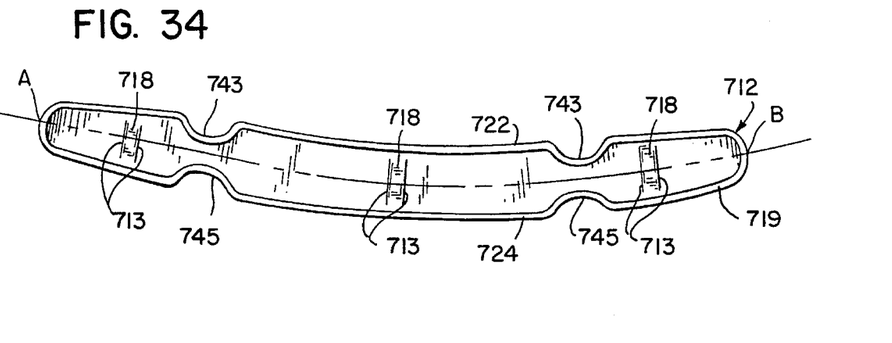
FIG. 34 is a plan view of a body of an alternate shape which could be used to practice the invention.

FIG. 34 illustrates an alternate shape of a belt body for practicing the invention, which may be applied to any of the aforementioned bodies or variations thereof. This body 712 has a pair of hip notches 743 cut into one edge and another pair 745 cut into the other edge. These help the body fit the shape of a human body more closely, to provide a cut-out for the hips, regardless of whether the body is being worn so that its conical shape opens up or opens down. Elements corresponding to the elements of the body 12 are labelled with the same reference number plus 700.

In addition, it should be noted that in its broadest scope the invention is not limited to any particular material for the belt body. The material may be a foam and fabric laminate as described above or in the patents incorporated herein by reference, or it may be another material, such as a foam and film laminate. What is contemplated here is a laminate of a foam material, which may be identical to that disclosed above, and a film which has a continuous surface, unlike a woven fabric in which the surface is broken by the interstitial spaces between the threads of the fabric. Such film would probably be applied to the outer surface of the foam instead of a fabric covering, with the usual fabric covering laminated on the inner surface.

Such films include polypropylene, polyester, ethylene vinyl acetate other polymeric materials and also films or foils of non-polymeric materials such as metal or cellulose. An advantage of using such continuous surface materials is that they can be readily printed or painted with high resolution graphics or finishes, such as metallic or holographic finishes or images, which are not readily obtainable with fabrics. Such films or foils can be laminated to a foam or other core using conventional techniques, such as heat laminating or a hot or cold lamination process using an adhesive. Moreover, the core need not be foam, but could, for example, be a three dimensional fabric material such as that which is commercially available from Synthetic Industries, Lumite Division, Norcross, Ga., under Style No. 60617000 or under Style No. 60645000. A support belt utilizing this material is disclosed in commonly owned U.S. Pat. Application Ser. No. 08/056,342 filed Apr. 30, 1993, which has been allowed and is hereby incorporated by reference. It should also be noted that such three dimensional fabric material could be incorporated in a body without any fabric coverings on either the inside or the outside surfaces.

Many other modifications and variations to the preferred embodiments described will be apparent to those skilled in the art. For example, the invention is not limited to the particular type of cinching system disclosed utilizing a ring and hook and loop type fastener material, but could use a different system, such as one of the systems disclosed in the aforementioned patents. Therefore, the invention should not be limited to the embodiments described, but should be defined by the claims which follow.

I claim:

1. In a support belt for wearing around the waist of a human body of the type having a body with an inner surface, an outer surface and longitudinal side edges connecting said inner and outer surfaces, and a cinching strap narrower than said body and having an inner surface, an outer surface and longitudinal side edges connecting said inner and outer surfaces for encircling said body when said belt is worn around the waist of a human body, the improvement wherein;

said longitudinal side edges of said body are arcuate over the length of said body and curve in the same direction;

said strap can be detachably removed from said body; and said strap includes at least two inextensible and straight strips joined end to end by an intermediate bridging section which is flexible so as to allow said strips to form an angle relative to one another as said strips lay against said body.

2. The improvement as claimed in claim 1, wherein said body is provided with belt loops on its exterior surface.

3. The improvement as claimed in claim 1, wherein said bridging section is a piece of fabric material.

4. The improvement as claimed in claim 3, wherein said bridging section is elastic.

5. The improvement as claimed in claim 3, wherein said bridging section is tubular.

6. The improvement as claimed in claim 1, wherein said strap is detachably secured to said exterior surface of said body by hook and loop fastener material.

7. The improvement as claimed in claim 1, wherein said body is provided with axially spaced laterally extending lines of perforation which define belt loops between them for securing said strap.

8. The improvement as claimed in claim 7, wherein said inner surface of said strap is provided with detachable fastener material.

9. The improvement as claimed in claim 8, further comprising a lumbar pad which is detachably securable to said detachable fastener material on said inner surface of said strap.

10. The improvement as claimed in claim 1, wherein sections of said body are laterally articulatable relative to each other.

11. The improvement as claimed in claim 10, wherein said body includes 5 sections including two end sections and a central section and two sections joining the end sections to the central section, said two sections being made of a material which is more flexible than the material of said end sections and central section.

12. The improvement of claim 11, wherein said material is an elastic fabric.

13. The improvement of claim 11, wherein said material is a polymeric foam material molded in the shape of accordion folds.

14. The improvement of claim 1, wherein said body has a pair of hip notches formed in each of said longitudinal side edges, one said pair being laterally opposite from the other pair.

15. The improvement of claim 1, wherein said body is made from a polymeric foam material and belt loops are molded into said body.

16. The improvement of claim 1, wherein belt loops are provided in said body by plastic molded belt loop halves which when placed together sandwich material of said body between peripheral flanges of said halves, said halves defining slots through which said strap may be threaded.

* * * * *